United States Patent [19]
Johnson, Jr.

[11] Patent Number: 5,125,400
[45] Date of Patent: Jun. 30, 1992

[54] ANKLE BRACE HAVING MULTIPLE INFLATABLE AIRCELLS

[75] Inventor: Glenn W. Johnson, Jr., Summit, N.J.

[73] Assignee: Aircast Incorporated, Summit, N.J.

[21] Appl. No.: 794,856

[22] Filed: Nov. 21, 1991

Related U.S. Application Data

[63] Continuation of Ser. No. 668,792, Feb. 25, 1991, abandoned, which is a continuation of Ser. No. 522,069, May 11, 1990, abandoned, which is a continuation of Ser. No. 363,410, May 31, 1989, abandoned, which is a continuation of Ser. No. 87,567, Aug. 14, 1987, abandoned, which is a continuation-in-part of Ser. No. 809,198, Dec. 16, 1985, abandoned.

[51] Int. Cl.⁵ .......................... A61F 3/00; A61F 5/00
[52] U.S. Cl. .................. 602/13; 128/DIG. 12; 128/DIG. 20; 602/27
[58] Field of Search .......... 128/80 H, 80 R, DIG. 12, 128/DIG. 20

[56] References Cited

U.S. PATENT DOCUMENTS

| | | | |
|---|---|---|---|
| 1,602,454 | 10/1926 | Riddell | 2/267 |
| 2,379,497 | 7/1945 | Sellmeyer | 128/24 R |
| 2,651,302 | 9/1953 | Berry . | |
| 2,694,395 | 11/1954 | Brown | 128/87 R |
| 2,781,041 | 2/1957 | Weinberg | 128/24 R |
| 3,548,809 | 12/1970 | Conti | 128/64 |
| 3,701,349 | 10/1972 | Larson | 128/82.1 |
| 3,811,434 | 5/1974 | Jacobson et al. | 128/89 R |
| 3,873,997 | 4/1975 | Gooding | 2/3 R |
| 3,955,565 | 5/1976 | Johnson, Jr. | 128/89 R |
| 4,157,713 | 6/1979 | Clarey | 128/87 R |
| 4,190,286 | 2/1980 | Bentley . | |
| 4,280,489 | 7/1981 | Johnson, Jr. | 128/166 |
| 4,338,923 | 7/1982 | Gelfer et al. | 128/24 R |
| 4,419,988 | 12/1983 | Mummert | 128/24 R |
| 4,500,019 | 2/1985 | Curley, Jr. . | |
| 4,521,166 | 6/1985 | Phillips . | |
| 4,700,403 | 10/1987 | Vacanti | 2/2 |

FOREIGN PATENT DOCUMENTS

| | | | |
|---|---|---|---|
| 4563179 | 4/1979 | Australia . | |
| 60614 | 3/1968 | Fed. Rep. of Germany | 128/DIG. 20 |
| 2913606 | 10/1979 | Fed. Rep. of Germany | 128/80 H |
| 2267751 | 12/1974 | France | 128/64 |
| 848028 | 7/1981 | U.S.S.R. | 128/64 |
| 852328 | 8/1981 | U.S.S.R. | 128/64 |
| 947772 | 1/1964 | United Kingdom | 2/413 |
| 1531268 | 11/1978 | United Kingdom | 128/89 R |

Primary Examiner—Edgar S. Burr
Assistant Examiner—Kimberly L. Asher
Attorney, Agent, or Firm—S. Michael Bender

[57] ABSTRACT

A pneumatic brace comprising at least one outer shell member and at least first and second pressurizable chambers juxtaposed therewith in an overlapping manner for providing a supporting cushion between said outer shell member and a body part or limb. One of said chambers is coextensive with substantially the entire inner surface of said one outer shell member for engagement with a corresponding portion of said body part or limb, while the other of said chambers is coextensive with a portion of said first chamber. In one preferred embodiment, the first and second chambers comprise separate inflatable airbags of different size disposed on said outer shell member with the smaller airbag positioned coextensively with the bottom portion of the larger airbag and between said larger airbag and said inner surface of said outer shell member. In alternatively preferred embodiments, the first and second chambers are integrally formed from a single inflatable liner having two compartments divided by a common wall, at least one of said compartments being selectively inflatable through integral valve means formed at least in part by said common wall.

9 Claims, 10 Drawing Sheets

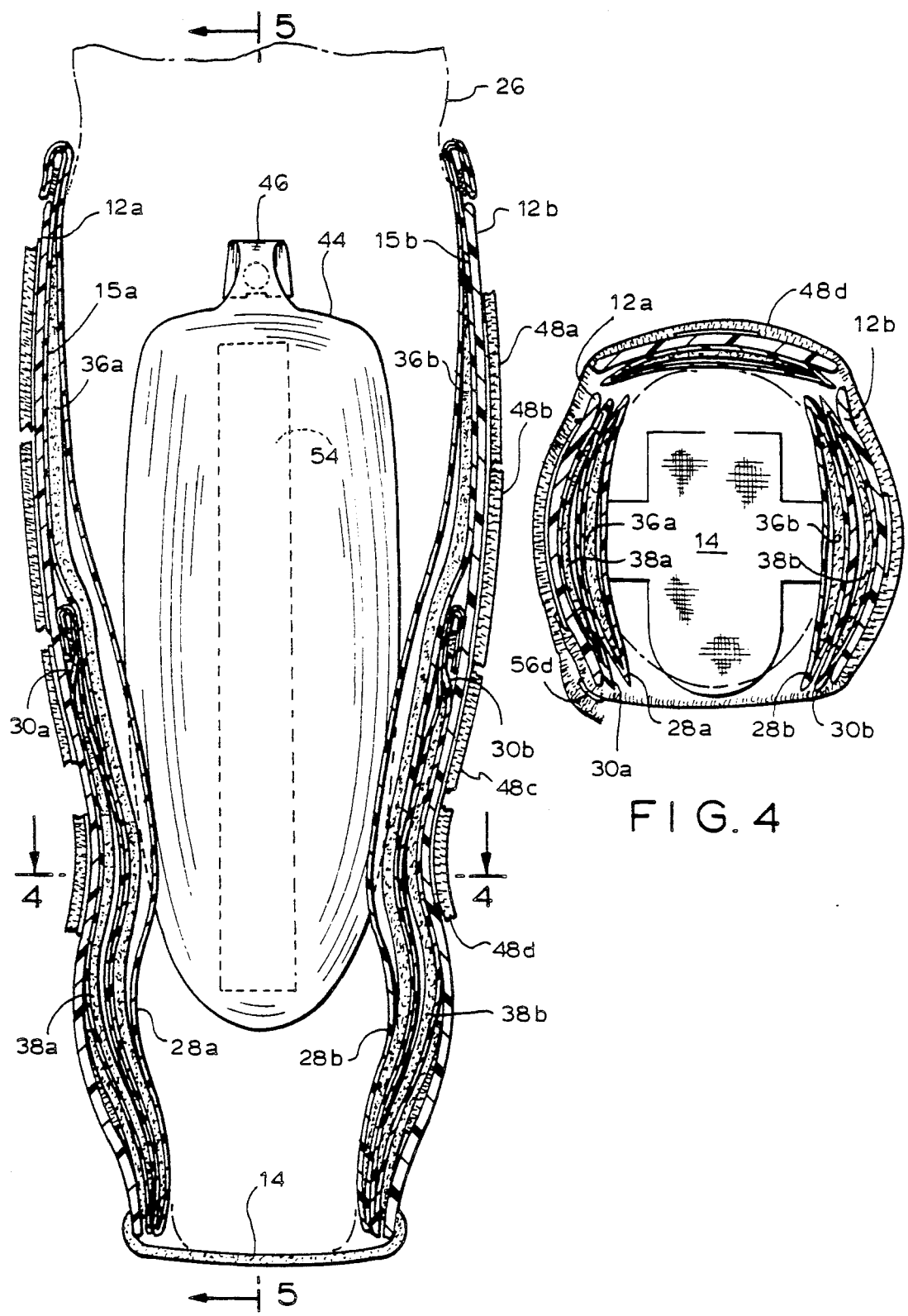

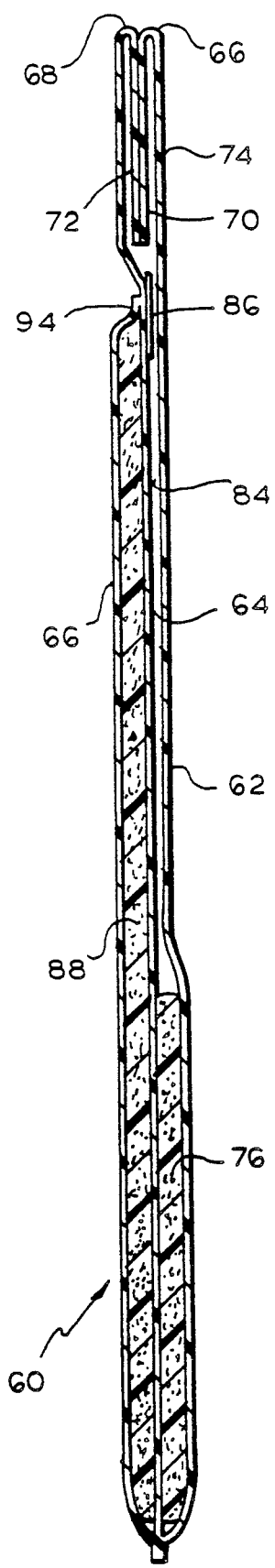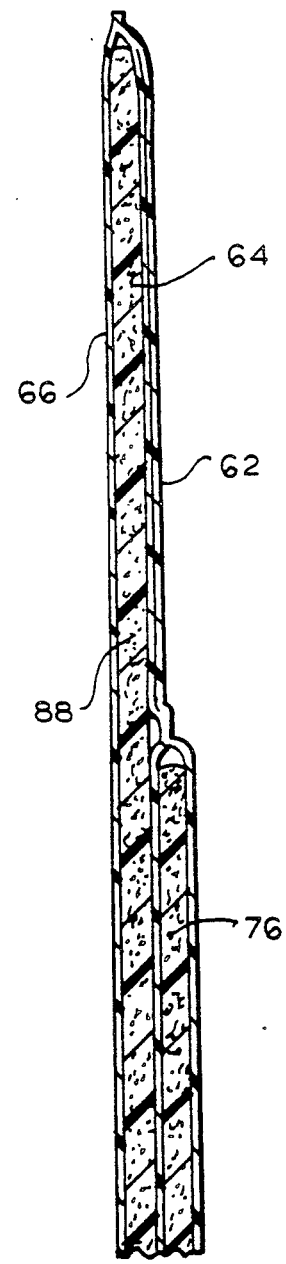
FIG. 8
FIG. 9

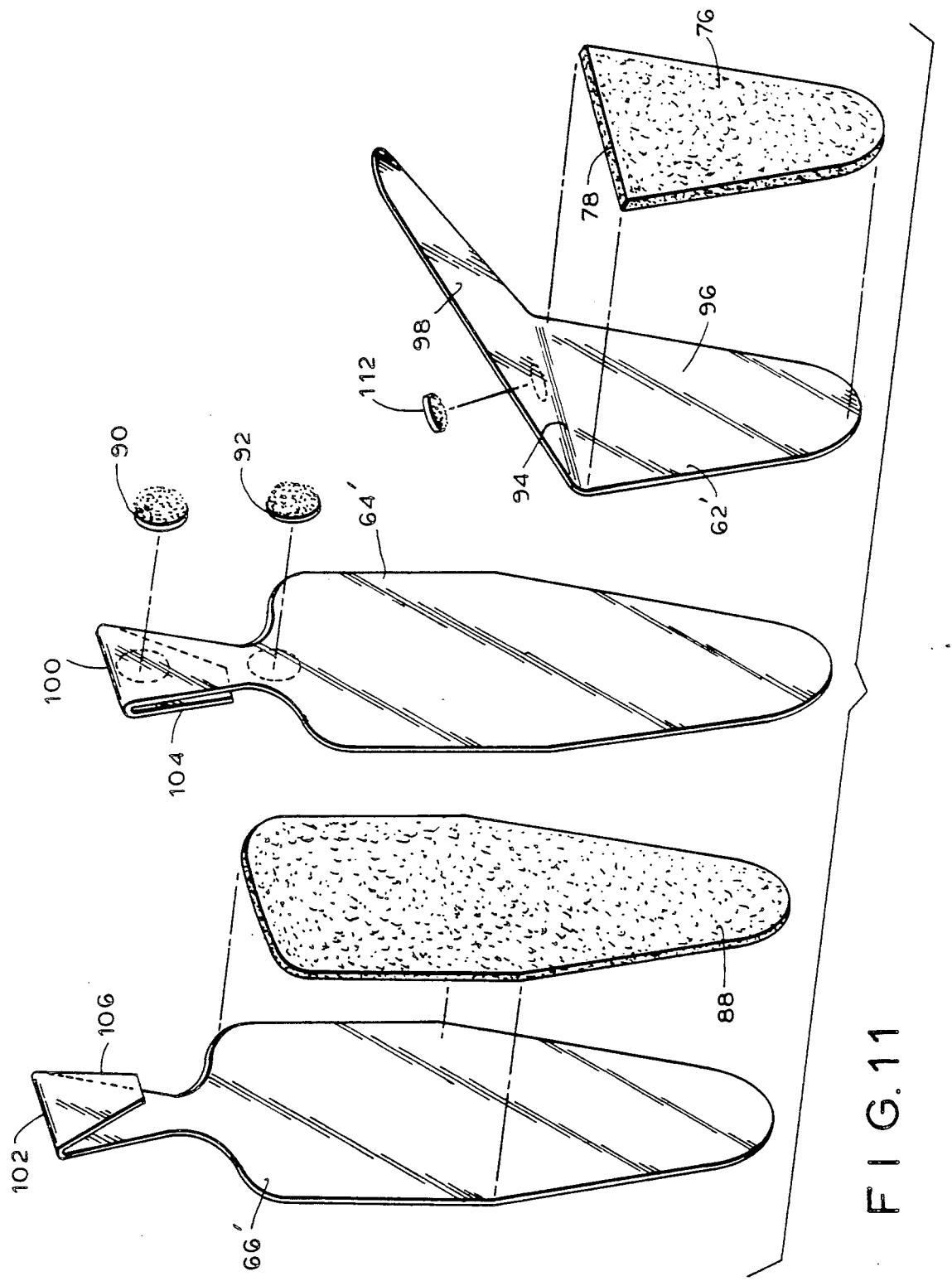

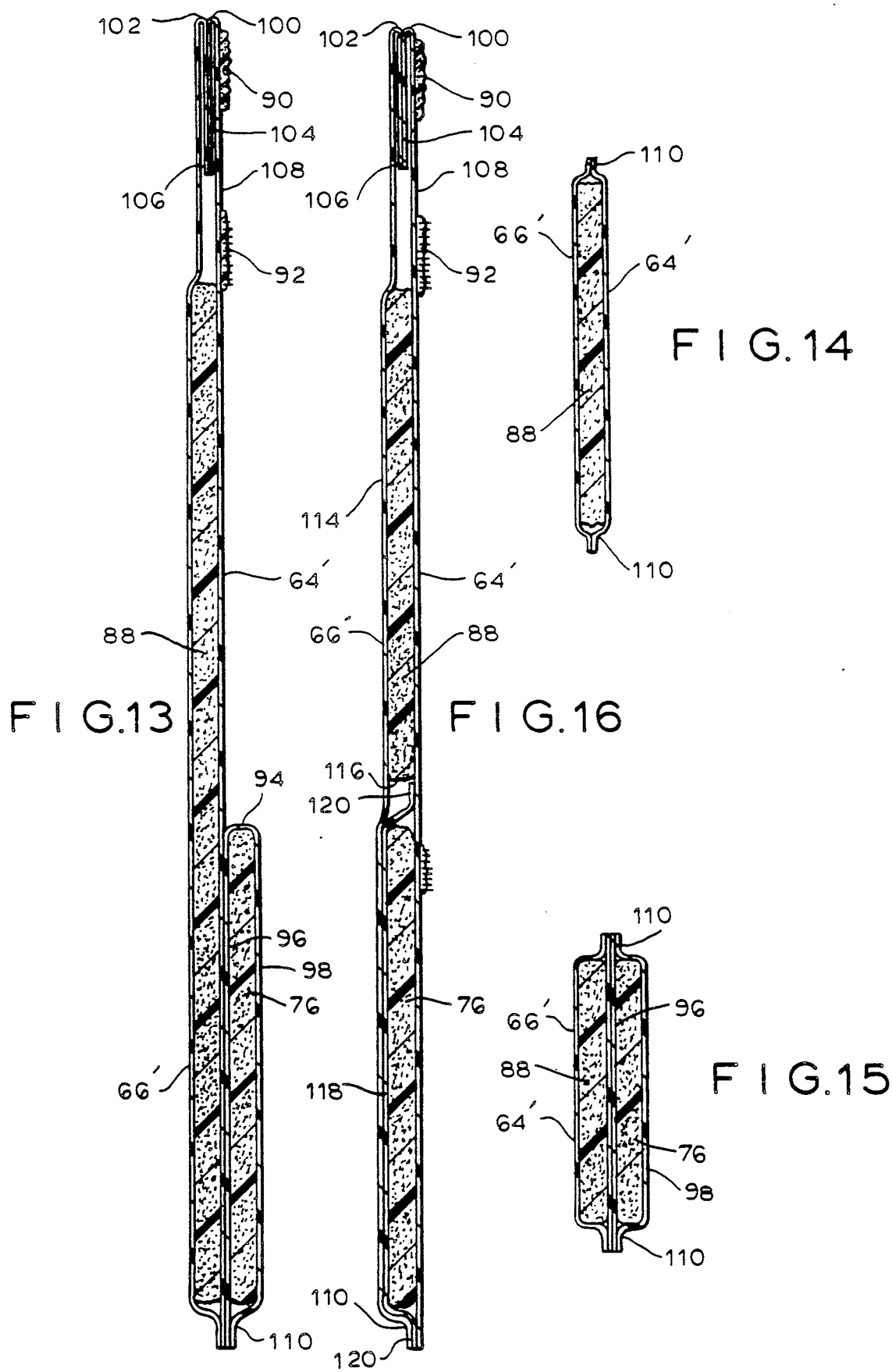

ANKLE BRACE HAVING MULTIPLE INFLATABLE AIRCELLS

RELATED APPLICATION

The present application is a continuation of application Ser. No. 07/668792, filed Feb. 25, 1991, now abandoned, which was a continuation of application Ser. No. 07/522069, filed May 11, 1990, now abandoned, which was a continuation of application Ser. No. 07/363410, filed May 31, 1989, now abandoned, which was a continuation of application Ser. No. 07/087567, filed Aug. 14, 1987, now abandoned, which was a continuation-in-part of Ser. No. 06/809198, filed Dec. 16, 1985, now abandoned.

FIELD OF INVENTION

The present invention relates generally to new and useful improvements in orthopedic braces, and more particularly, to improvements in pneumatic braces featuring one or more rigid outer shell members having associated therewith an inflatable liner or airbag for engaging a body part or limb.

BACKGROUND ART

Pneumatic braces of the foregoing type are fully disclosed in my prior U.S. Pat. No. 4,280,489 and prior pending U.S. patent application, Ser. No. 06/694,700, filed Jan. 25, 1985. Commercial embodiments of the pneumatic brace incorporating the inventions disclosed and claimed in my prior patent and application and adapted to be fitted about the lower leg typically comprise an outer shell member in the form of a U-shaped stirrup, inflatable liners or airbags disposed within the stirrup member in coextensive relation to the upstanding sidewalls thereof, and strap fastening means for maintaining the stirrup member sidewalls in engagement with confronting portions of the lower leg whereby each airbag serves as a firm supporting cushion of pressurized air between the irregular contours of the lower leg and the stirrup member sidewalls.

Because this brace construction is capable of stabilizing the ankle against eversion and inversion without restricting dorsiflexion and plantoflexion while being worn inside a conventional shoe, ambulatory functionality and permitted exercises are feasible thereby encouraging more rapid recovery from various injuries to the lower extremity, e.g. ankle sprains, than otherwise would be possible. As a result of these and other important advantages, the commercial embodiments referred to above which are marketed by AIRCAST INCORPORATED, Summit, N.J., have become widely accepted and recognized throughout the medical and orthopedic community. See for example, Ramey, H. and Jakob, R. P., "*Functional Treatment of Fresh Fibular Ligament Lesions Using the AIRCAST\* Ankle Brace*", Swiss Journal of Sports Medicine, 2-31:53-57, June, 1983; Stover, C. N. and York, J. M. "*AIRCAST/AIR-STIRRUP\* System For Graduated Management of Lower Extremity Injuries*", Scientific Exhibit Paper, American Association of Orthopedic Surgeons, San Francisco, 1979; Stover, C. N., "AIR-STIRRUP Management of Ankle Injuries in the Athlete", American Journal of Sports Medicine, 8-5:360-365, 1980; and Hamilton, W. G., "*Sprained Ankles in Ballet Dancers*", Foot and Ankle, 3-2:99-102, 1982. * AIRCAST is a trademark and AIR-STIRRUP is a registered trademark of AIRCAST INCORPORATED, Summit, N.J.

As disclosed in my prior '489 patent, column 6, lines 16-31, dorsiflexion of the ankle by a wearer of the patented pneumatic brace causes momentary increase in the internal pressure of each airbag. It is believed by at least some of the authors cited above that htis alternating pressure exerts a "milking effect" on edematous tissues during function which in turn, contributes to a more rapid recovery and/or reduction in swelling.

It has also been demonstrated by the JOBST COMPANY, Peoria, Ill., that treatment of lymphedema may be facilitated by the use of a compression stocking worn about the lower leg. The JOBST compression stocking enhances graduated application of pressure to the lower leg, i.e. relatively greater pressure is applied to the ankle region as opposed to that applied along portions of the lower extremity displaced above the ankle.

However, since the JOBST graduated compression stocking is elastic, it fails to provide sufficient pulsating pressure to achieve the desired pumping or milking effect during ambulatory function.

Certain disadvantages also persist with respect to the AIR-STIRRUP pneumatic brace described in my '489 patent. For example, if the bottom-most fastening straps proximal to the ankle are tightened first, the single airbag in each upstanding sidewall may be over compressed in the ankle region possibly resulting in uncomfortable contact between the bony portions of the ankle (i.e. the malleoli) and the outer hard shell of the brace. Further, in the leg brace version of the AIR-STIRRUP brace which has a greater longitudinal extent along the lower leg than does the ankle brace version, the magnitude of pressure pulsation is less because the larger volume of the airbag used in the leg brace vis-a-vis the ankle brace tends to attenuate compression due to dorsiflexion.

DISCLOSURE OF THE INVENTION

Against the foregoing background, it is a primary object of the present invention is to provide an improved pneumatic brace having means for overcoming the aforementioned disadvantages.

It is another object of the present invention to provide an improved pneumatic brace having means for applying a graduated application of pressure to the lower leg, i.e. greater supporting pressure in the ankle region relative to that applied against portions of the leg displaced above the ankle.

Toward the accomplishment of these and additional objects and advantages, the pneumatic brace of the present invention briefly described comprises at least one outer shell member and at least first and second pressurizable chambers juxtaposed therewith in an overlapping manner for providing a supporting cushion between said outer shell member and a body part or limb. One of said chambers is coextensive with substantially the entire inner surface of said one outer shell member for engagement with a corresponding portion of said body part or limb, while the other of said chambers is coextensive with a portion of said first chamber. In one preferred embodiment, the first and second chambers comprise separate inflatable airbags of different size disposed on said outer shell member with the smaller airbag positioned coextensively with the bottom portion of the larger airbag and between said larger airbag and said inner surface of said outer shell member. In alternatively preferred embodiments, the first and second chambers are integrally formed from a single inflatable liner having two compartments divided by a common wall, at least one of said compartments being selectively inflatable through integral valve means formed at least in part by said common wall.

BRIEF DESCRIPTION OF DRAWINGS

The preceeding and still further features and advantages of the present invention as well as a more complete understanding thereof will be made apparent from a study of the following detailed description of the invention in connection with the accompanying drawings wherein:

FIG. 3 is a sectional view in elevation of the embodiment of FIG. 1 assembled together and fitted about the aforesaid imaginary lower extremity taken along line 3—3 of FIG. 2;

FIG. 4 is a sectional view taken along line 4-4 of FIG. 3;

FIG. 8 is a sectional view taken along line 8—8 of FIG. 7;

FIG. 9 is a sectional view taken along line 9—9 of FIG. 7;

FIG. 11 is a diagramatic exploded, perspective view of yet another alternatively preferred embodiment of the present invention comprising an integral, dual-chamber airbag;

FIG. 13 is a sectional view taken along line 13—13 in FIG. 12;

FIG. 14 is a sectional view taken along line 14—14 in FIG. 12;

FIG. 15 is a sectional view taken along line 15—15 in FIG. 12; and

FIG. 16 is a sectional view taken along line 13—13 of FIG. 12, but showing a slightly modified version of the alternatively preferred embodiment of FIG. 11.

BEST MODE OF CARRYING OUT THE INVENTION

Figure 1:
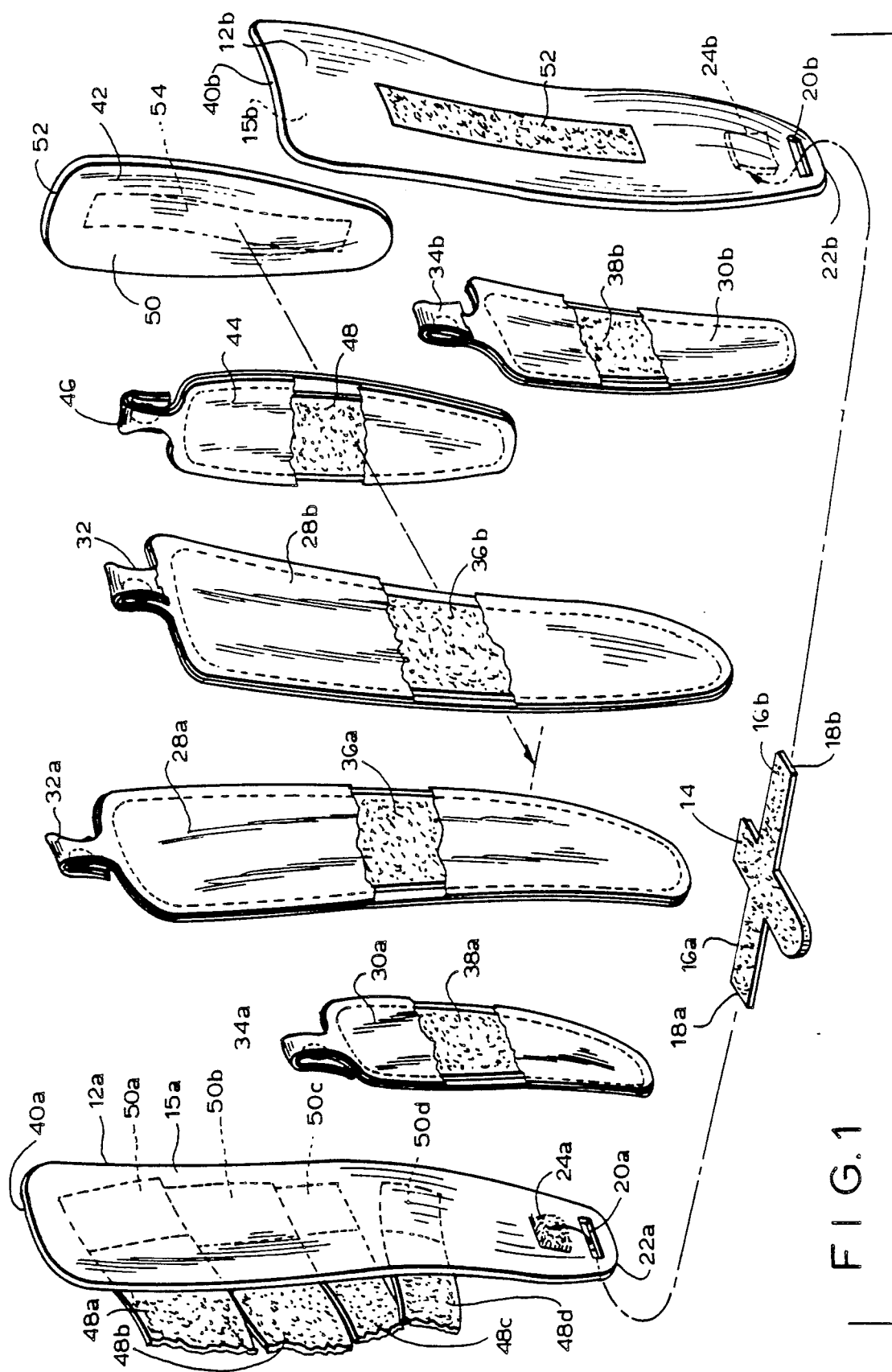
FIG. 1 is a diagramatic, exploded, perspective view of a first preferred embodiment of the present invention.
Figure 2:
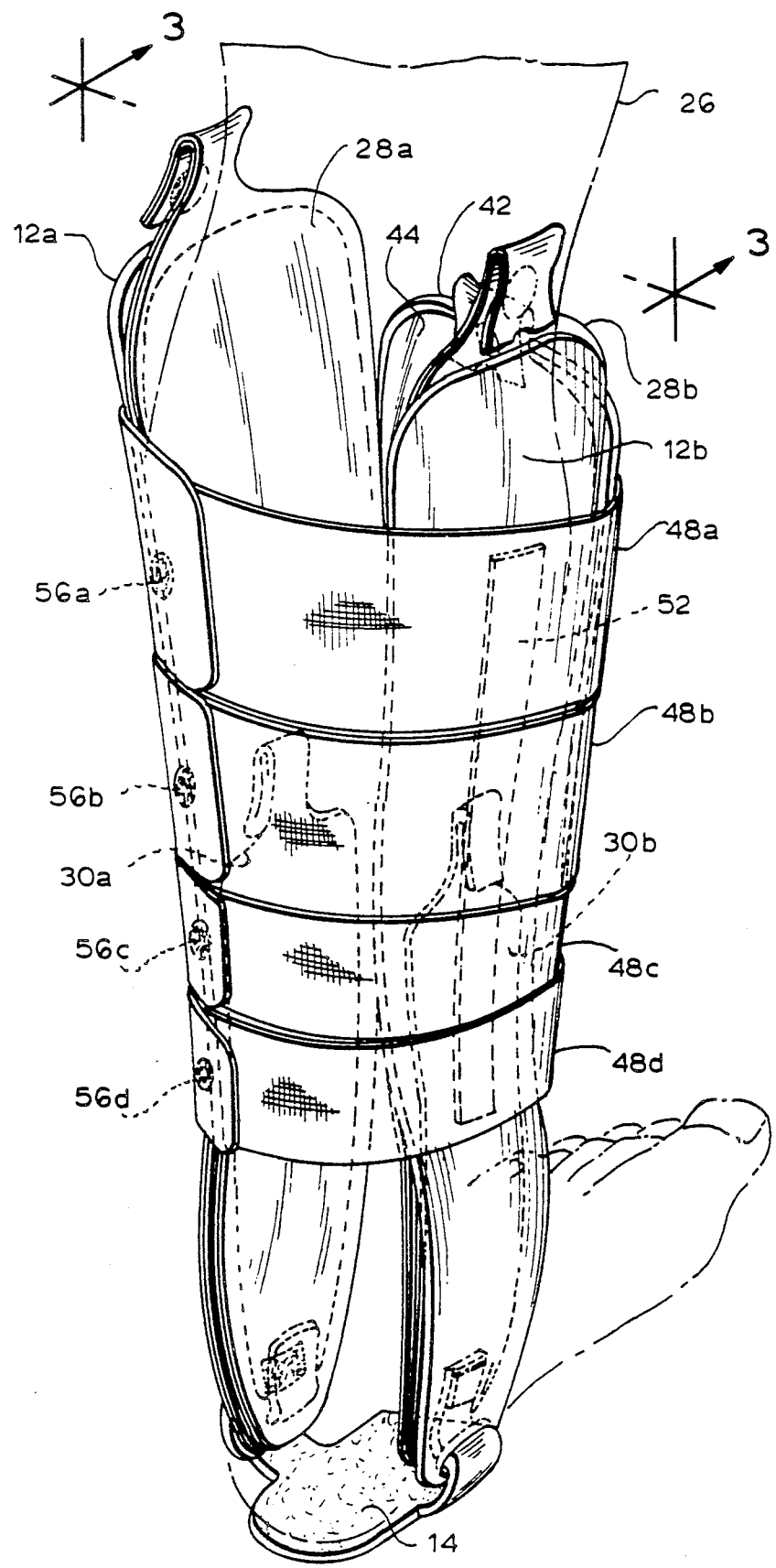
FIG. 2 is a schematic, perspective view of the embodiment of FIG. 1 assembled and fitted about an imaginary lower extremity of a human.

Turning initially to FIGS. 1 and 2, a first preferred embodiment of the present invention comprises a pneumatic brace generally represented by reference numeral 10 similar in many respects to the pneumatic brace described in my prior U.S. Pat. No. 4,280,489 and copending U.S. patent application, Ser. No. 06/694,700, filed Jan. 25, 1985, the disclosure of each of which is hereby incorporated into the present specification by this reference and made part hereof. Thus, brace 10 in its initial preferred form is adapted to be fitted about the lower extremity of a human and comprises a pair of outer shell members 12a, 12b preferably of a stiff, durable, molded plastic material generally shaped to conform to the lateral and medial sides of the lower extremity, respectively, and a base member 14 having a pair of oppositely extending, hinge portions 16a, 16b. Preferably, the base member 14 and hinge portions 16a, 16b are formed from a common piece of flexible woven mylon material cut to size and shaped substantially as shown, and have bonded thereto a layer of fastener material such as that commonly sold under the VELCRO trademark.

Figure 5:
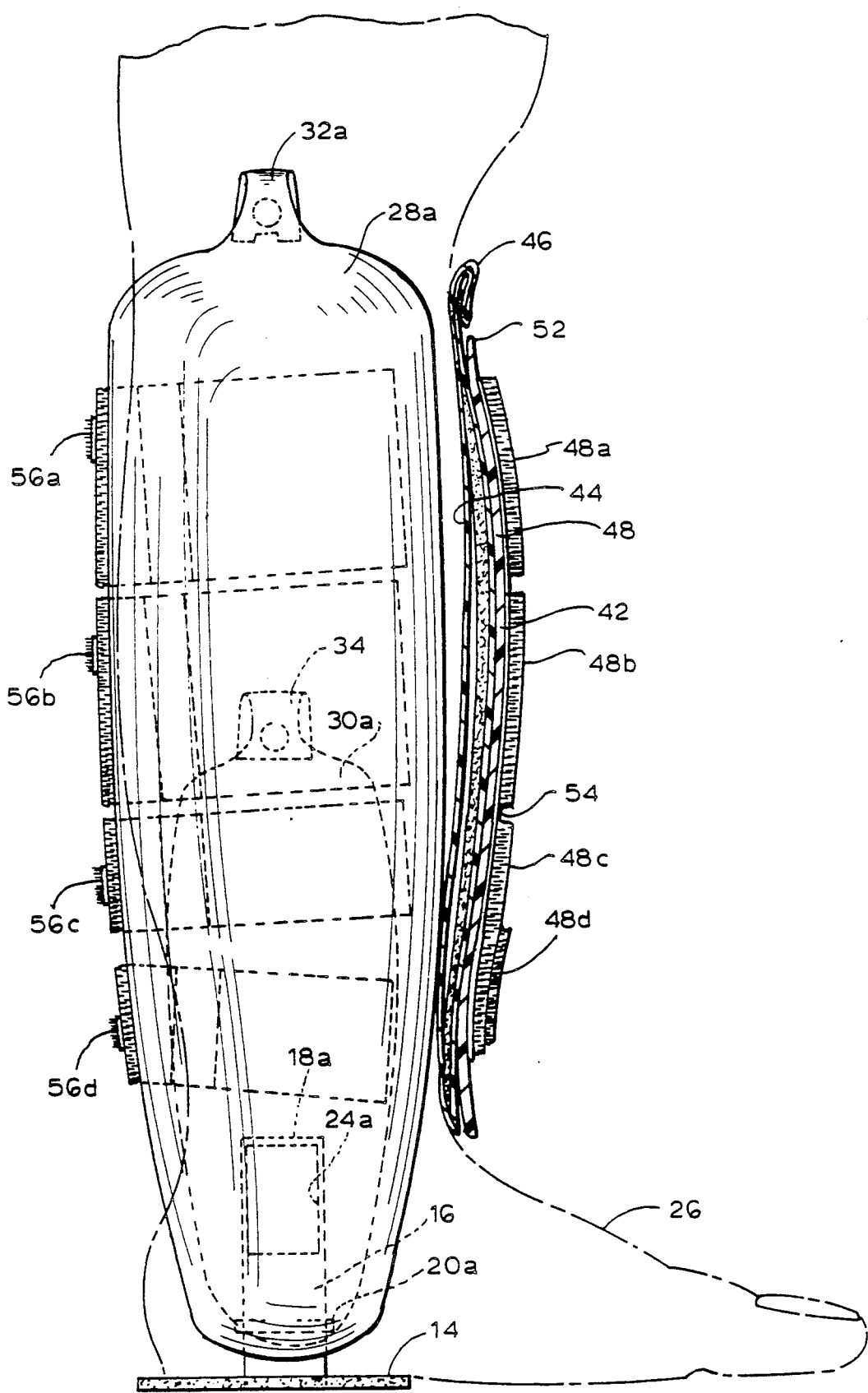
FIG. 5 is a sectional view taken along line 5-5 of FIG. 3.

As best seen in FIGS. 3 and 5, the distal ends 18a, 18b of hinge portions 16a, 16b are adapted to be inserted through transverse slots 20a, 20b proximal to the lower edges 22a, 22b of shell members 12a, 12b and thereupon be fastened to a pair of mating VELCRO fastener patch elements 24a, 24b in slightly spaced relation above slots 20a, 20b, preferably by means of a suitable adhesive. It will be apparent that when the shell members and the base portion are so assembled, there is formed a U-shaped stirrup member adapted to be fitted about the lower extremity with the heel of the foot resting upon the base member and the opposed shell members forming a pair of upwardly extending sidewall portions adapted to be flexed or displaced via hinge portions 16a, 16b into confronting engagement with corresponding opposed side portions of the lower extremity substantially as depicted in FIGS. 2 and 5 with the lower extremity (i.e. the right leg, ankle, and foot of a human) being indicated schematically by broken line 26.

In my patented pneumatic brace, there is provided a single flexible, inflatable airbag or liner on the inwardly facing surface of each sidewall member. In accordance with the present invention, the initial preferred embodiment disclosed herein departs significantly from this prior arrangement by featuring a pair of separate, differently size, flexible, inflatable airbags 28a, 28b and 30a, 30b disposed in a juxtaposed, overlapping manner on the inwardly facing, confronting surfaces of sidewall members 12a, 12b substantially as shown in FIGS. 3-5.

Thus, sidewall member 12a has associated therewith a first inflatable airbag 28a which extends substantially coextensively with respect to the inner surface 15a of sidewall member 12a, and a second inflatable airbag 30a which extends substantially coextensively with respect to approximately the bottom half of both the inner surface 15a and the corresponding confronting surface of airbag 28a, i.e. airbag 30a is about one half as large as airbag 28a, is disposed between sidewall member 12a and airbag 28a, and is substantially coextensively aligned with approximately the bottom half portion of airbag 28a.

Likewise, sidewall member 12b has associated therewith a first inflatable airbag 28b extending substantially coextensively with respect to the inner surface 15b of sidewall member 12b, and a second inflatable airbag 30b extending substantially coextensively relative to approximately the bottom half of both the inner surface 15b and the corresponding confronting surface of airbag 28b, i.e. airbag 30b is approximately half the size of airbag 28b, is positioned between sidewall member 12b and airbag 28b, and is substantially coextensively aligned with approximately the bottom half portion of airbag 28b.

The inflatable, flexible liners or airbags 28a, 28b, 30a, 30b adapted for use with the initial embodiment of this invention preferably are the same type fully described in my copending patent application, Ser. No. 06/694,700, filed Jan. 25, 1985, (incorporated herein). Hence, each airbag comprises a pair of similarly sized, opposed, thin sheets of pliable material (e.g. vinyl plastic) bonded together along their confronting peripheries using known joining techniques such as heat or electronic bonding, for example. As more fully disclosed in my co-pending application (and my prior U.S. Pat. No. 4,276,920, entitled "Self Sealing Valve", incorporated therein), each such airbag 28a, 28b, 30a, 30b further includes an integral valve 32a, 32b, 34a, 34b extending upwardly therefrom and having a normally sealed throat through which a flexible plastic tube (not shown) may be inserted to facilitate selective inflation or pressurization of eah airbag via mouth entubation. Also, each valve may carry exteriorly a pair of spaced, cooperating VELCRO fastener elements to enable the valve to be folded down upon itself and fastened in place thereby presenting a neater appearance and helping to avoid leakage of air through the throat of each valve. It will be appreciated that the invention is not limited to this particular valve construction and other conventional one-way valves for selectively admitting and/or exhausting air to and from the interior of each inflatable airbag may be utilized instead.

In addition, and as also more fully described in my copending application cited above, each airbag preferably is preinflated by having inserted therein during fabrication a filler member or pad 36a, 36b, 38a, 38b of compressible, resilient, porous material, preferably open cell urethane foam, shaped and sized to substantially completely fill the interior volume of each airbag, respectively, although here again it will be understood that such filler members are not necessary for practicing and/or achieving the advantages of the present invention.

Thus, whether or not the airbags are pre-inflated employing filler members 36a, 36b, 38a, 38b, they preferably are affixed to the opposed, inwardly facing surfaces 15a, 15b of sidewall members 12a, 12b through suitable application of a conventional adhesive liquid compound (or mating VELCRO fastener elements) such that the attached airbags 28a, 28b substantially entirely overlap attached airbags 30a, 30b; the integral values 32a, 32b of airbags 30a, 30b extend above the upper edges 40a, 40b of sidewall members 12a, 12b; and the overlapping lower portions of the airbags, in turn, overlap the attached distal ends 18a, 18b of the base member's hinge portions 16a, 16b as most clearly depicted in FIGS. 2-5. The adhesive compound, if employed, should be of the well known "tacky" variety which when dry permits airbags 28a, 28b to be peeled away from the inner surfaces 15a, 15b of shell members 12a, 12b as desired to permit access to the integral valves, 34a, 34b on the smaller sized airbags 30a, 30b, and then reattached. In similar fasion, the bottom portions of airbags 30a, 30b may be peeled back as desired to permit adjustment between VELCRO fastener elements 24a, 24b and hinge end portions 18a, 18b, and then reattached.

In accordance with another feature of the present invention, an optional shin guard may be provided in the form of outer shell member 42 fabricated of the same material as sidewall wall members 12a, 12b and shaped to generally conform to the curvature of the anterior portion of the lower extremity. The shin guard preferably includes a single inflatable airbag or liner 44 substantially identical to the construction of airbags 28a, 28b, 30a, 30b, i.e. it preferably features an integral valve 46 and preinflation filler pad 48; is sized to coextensively overlie substantially the entire inwardly facing surface 50 with integral valve 46 extending above upper edge 52; and is releaseably attached to surface 50 using a suitable adhesive compound applied thereto or a pair of mating VELCRO fastener elements.

As is evident from the above description, the assembled leg brace of FIGS. 1-5 is intended to be fitted about the lower extremity of a human with the sidewall members 12a, 12b flexed or displaced toward and into engagement with corresponding confronting medial and lateral portions of the foot, ankle and lower leg. In addition, the shin guard is intended to be fitted to engage a corresponding confronting portion of the anterior of the lower leg above the ankle. By such arrangement, airbags 28a, 30a, 28b, 30b and 40 will be compressed sufficiently to provide a pressurized air cushion or envelope circumferentially engaging the lower extremity and filling the voids between the inner surfaces of the upstanding sidewall members and the shin guard on the one hand, and the irregular contours of the lower extremity on the other hand.

In order to maintain this desired relationship and the appropriate magnitude of pressurization inside the airbags, the upstanding sidewalls and shin guard advantageously are fastened together and maintained in position relative to the lower extremity by a plurality of elongated, circumferentially extending, longitudinally spaced, flexible fastening straps 48a-d (shown partially broken away in FIG. 1).

Preferably, each strap 48a-d is fabricated of the same well known woven nylon material as base member 14 and therefore includes a layer of VELCRO fastening material on the underside thereof as viewed in FIGS. 1-5. Each strap is securely affixed to or terminates in a respective VELCRO fastener patch element 50a-d which, in turn, is securely attached to the outer surface of shell member 12b, preferably by means of a suitable adhesive, with the patch elements being adapted to securely mate with the VELCRO fastening material on the underside of each strap member. Thus, in the preferred arrangement, one end of each strap member 48a-d has its corresponding patch element 50a-d anchored to shell member 12a thereby permitting the underside of the other or distal free end of each strap member to be securely fastened to such corresponding fastener patch element after the strap members are circumferentially drawn and tensioned snuggly about the exterior of both shell members and the shin guard. Additional longitudinally extending VELCRO fastener elements 52, 54 preferably attached respectively to the outer surface of shell member 12b and shin guard member 42, as well as disc-shaped VELCRO fasteners 56a-d attached to the outer surface of straps 46a-d as depicted, may be provided to further matingly engage the portions of the underside of strap members 48a-d in circumferential contact therewith when the strap members are tightened and fastened about the shell members and shin guard. Fastener elements 56a-d are so located along the axis of each corresponding strap 46a-d so that when the latter are circumferentially drawn about the leg brace as shown in FIG. 2, the undersides of the straps will matingly engage fasteners 56a-d near the distal extremity of each strap preventing the free ends of the straps from dangling in a loose fasion and thus, maintaining a neat appearance.

In practice, leg brace 10 is fitted about the lower extremity by positioning the leg between the shell members 12a, 12b with the heel of the foot resting upon base member 14, and putting on but not yet lacing the shoe to be worn with the leg brace. The next step is to squeeze or flex the outer shell members 12a, 12b toward each other into engagement with the lower extremity. The bottom-most fastener strap 48d then is circumferentially drawn (tensioned) about both shell members until comfortable, but not excessive compression of the overlapping airbags 28a, 28b and 30a, 30b is achieved in the region of the ankle whereupon the strap is fastened in place via mating patch elements 50d and 56d. The shoes should then be laced up.

If the optional shin guard is to be worn, it should be positioned on the anterior portion of the leg with its bottom edge underneath the bottom fastener strap 48d and the shin guard's side edges under the adjacent side edges of shell members 12a, 12b, respectively, before the bottom strap is secured. The upper strap 48a should then be circumferentially drawn about the shell members and shin guard until these parts are comfortably engaging the leg, then fastened in place by engagement with the mating VELCRO fastener elements 50a, 52, 54 and 56a.

Finally, and in similar fashion, the two remaining middle fastening straps, 48b, 48c are circumferentially tensioned in place and fastened.

As described above, the bottom strap 48d should be fastened more snuggly or under greater tension than the other straps 48a-c. Since the air inside the larger airbags is displaced upwardly, this helps to assure that the smaller airbags 30a, 30b are placed under sufficient compression to have greater internal pressurization than the larger airbags 28a, 28b, thus achieving the desired graduated compression. That is, greater supporting pressure is applied in the region of the ankle coextensive with airbags 30a, 30b (see FIG. 3) than is applied in the region above and displaced from the ankle coextensive with the upper half of the larger airbags 28a, 28b.

The desired graduated compression arrangement is further facilitated by initially inflating or pre-inflating the larger airbags 28a, 28b to a relatively lesser extent than the smaller airbags 30a, 30b. If the pre-inflation filler members according to the teachings in my prior co-pending application, cited above, are utilized as preferred, this is accomplished by providing filler members 38a, 38b having a greater transverse thickness as measured in the plane of FIGS. 2 and 4 than that of filler members 36a, 36b.

Thus, without limiting the present invention, I have found that excellent results are achievable with a leg brace having outer shell members 16 inches in longitudinal extent, 3.5 inches in transverse extent (maximum), a size ratio of about 2:1 between the larger airbags and the smaller airbags, and preinflation filler members having normal (uncompressed) transverse thicknesses measured in the plane of FIGS. 4 and 5 of 0.150 inches (larger airbags) and 0.225 inches (smaller airbags), respectively.

Actual experimentation with the foregoing leg brace embodiment under ambulatory conditions was undertaken using pressure transducers attached to each airbag and suitable recording means. It was discovered that in response to dorsiflexion of the ankle the internal pressure of the smaller airbag varied in the range between about 30 mm Hg. (static) to about 60 mm Hg. whereas the internal pressure of the larger airbag varied in the range between about 25 mm Hg. (static) to about 40 mm Hg. It will thus be appreciated that the use of the supplemental smaller airbags 30a, 30b as contemplated by the present invention achieves both graduated compression and pulsating pressure during ambulation as desired.

It also will be noted with particular reference to FIG. 3 that the disclosed arrangement featuring the smaller airbags 30a, 30b in a location proximal to the bony regions of the ankle (i.e. the malleoli) as substantially illustrated helps to avoid uncomfortable contact between these body parts and the hard outer shell members by focusing maximum supporting pressure only in the ankle region. If a single airbag were employed as in the prior arrangement, inflation to a pressure high enough to avoid contact in the ankle region would cause excessive pressure elsewhere.

While it is true that in the preferred embodiment, the smaller airbags 30a, 30b are placed between the larger airbags 28a, 28b and each outer shell member respectively, it will be understood that this arrangement is not essential, but merely desirable as it affords contact between portions of the leg and the smoother, continuous surface of the larger airbags 28a, 28b rather than the upper extremity and valve of the smaller airbags which would present an interrupted surface in engagement with the leg. Therefore, the present invention should not be so limited to the arrangement illustrated, i.e. in theory, the smaller airbags may be placed between the two lower portions of the larger airbags and the portions of the leg coextensive therewith and still deliver the advantages of graduated compression and pulsating pressure described above.

A subject wearing the leg brace 10 of FIGS. 1-5 may find it necessary from time to time to increase pressurization of the airbags and/or provide more comfort after the initial fitting. Such readjustment may easily be effected by releasably disengaging the bottom strap with one hand and flexing the opposed outer shell sidewall members toward one another sufficiently with the other hand. The bottom strap may then be refastened followed by similar readjustment of the remaining straps.

If yet additional final adjustment for added comfort or support is required, this may be accomplished by unfastening the leg brace and further inflating one or more airbags 28a, 28b, 30a, 30b 42 by inserting a plastic tube into the throat of valves 32a, 32b, 34a, 34b, 46 and using mouth entubation. As mentioned above, access to valves 34a, 34b for supplemental inflation of airbags 30a, 30b is achieved by peeling back overlapping airbags 28a, 28b, effecting the desired increase in internal pressure via mouth entubation, and then reattaching airbags 28a, 28b to their original position.

Also, it will be observed that the width of base member 14 and the spacing between the shell members 12a, 12b may be adjusted to fit lower extremities of varying size by peeling back the overlapping bottom portions airbags 28a, 28b, and 30a, 30b, releasing the attachment between distal portions 18a, 18b of hinge portions 16a, 16b and VELCRO fasteners 24a, 24b, reattaching as desired, and restoring the overlapping airbag bottom portions to their original position.

In its broadest terms, the preferred embodiment of FIGS. 1-5 features an outer shell member having two pressurizable chambers associated therewith, one chamber being coextensively related to the shell member and the other chamber being coextensively related to a portion of the first chamber. As applied to the embodiment of FIGS. 1-5, the first chamber corresponds to the larger airbags 28a, 28b whereas the other chamber corresponds to the smaller airbags 30a, 30b. I have found that the foregoing arrangement comprising a pair of separate inflatable airbags may yet still be further improved by employing the alternatively preferred embodiment illustrated in FIGS. 6-10.

More particularly. I have discovered that a unitary airbag or liner member having a pair of pressurizable chambers is less bulky, less expensive to fabricate, and is aesthetically more desirable than a pair of separate inflatable airbags as disclosed, for example, in connection with the initial preferred embodiment of FIGS. 1-5.

Thus, turning now to FIGS. 6-10 there is shown such a unitary member generally represented by reference numeral 60 comprising three relatively thin, sheets or plies 62, 64, and 66 coextensively joined or bonded together along their common peripheral extents to form a pair of pressurizable chambers interiorly thereof as will be explained in more detail below.

Each ply is fabricated from an air-impervious, tough, flexible material such as vinyl plastic, for example, and cut to the shape substantially as shown on a conventional die cutting press.

Plies 62, 64 are mirror images of one another and include integral extensions 62a, 64a projecting upwardly with respect to their topmost edges, respectively. The extensions 62a, 64a, in turn, are folded along creases 66, 68 to define a pair of confronting end flaps 70, 72. Thus, when plies 62, 64 are bonded together congruently in a manner more fully described in my prior '920 patent, the integral extensions 62a, 64a, and end flaps 70, 72 form a self-sealing valve member 74 (FIG. 7) adapted to seal any air in a first chamber formed interiorly of the joined plies, thus preventing loss of internal pressurization. As further taught in the '920 patent, integral valve 74 may selectively be opened as, for example, by a suitably sized plastic tube inserted between the confronting flaps to admit or exhaust air from the first chamber.

Figure 6:
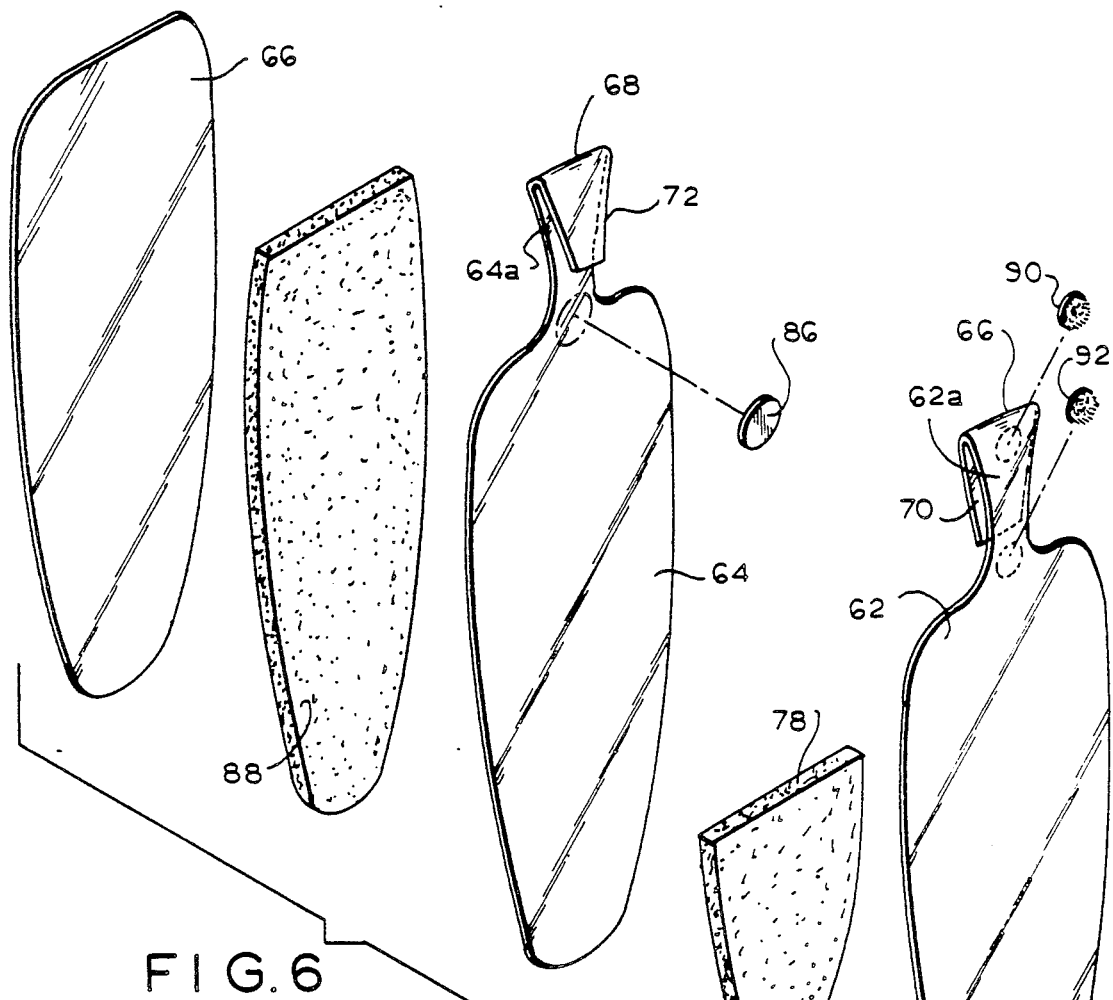
FIG. 6 is a diagramatic, exploded, perspective view of an alternatively preferred embodiment of the present invention comprising an integral, dual-chamber airbag.
Figure 10:
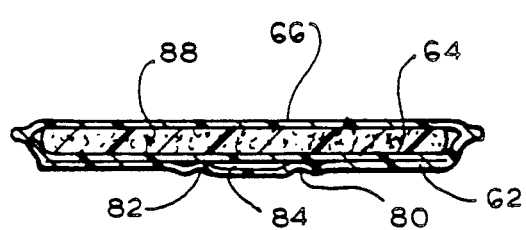
FIG. 10 is a sectional view taken along line 10—10 of FIG. 7.
Figure 7:
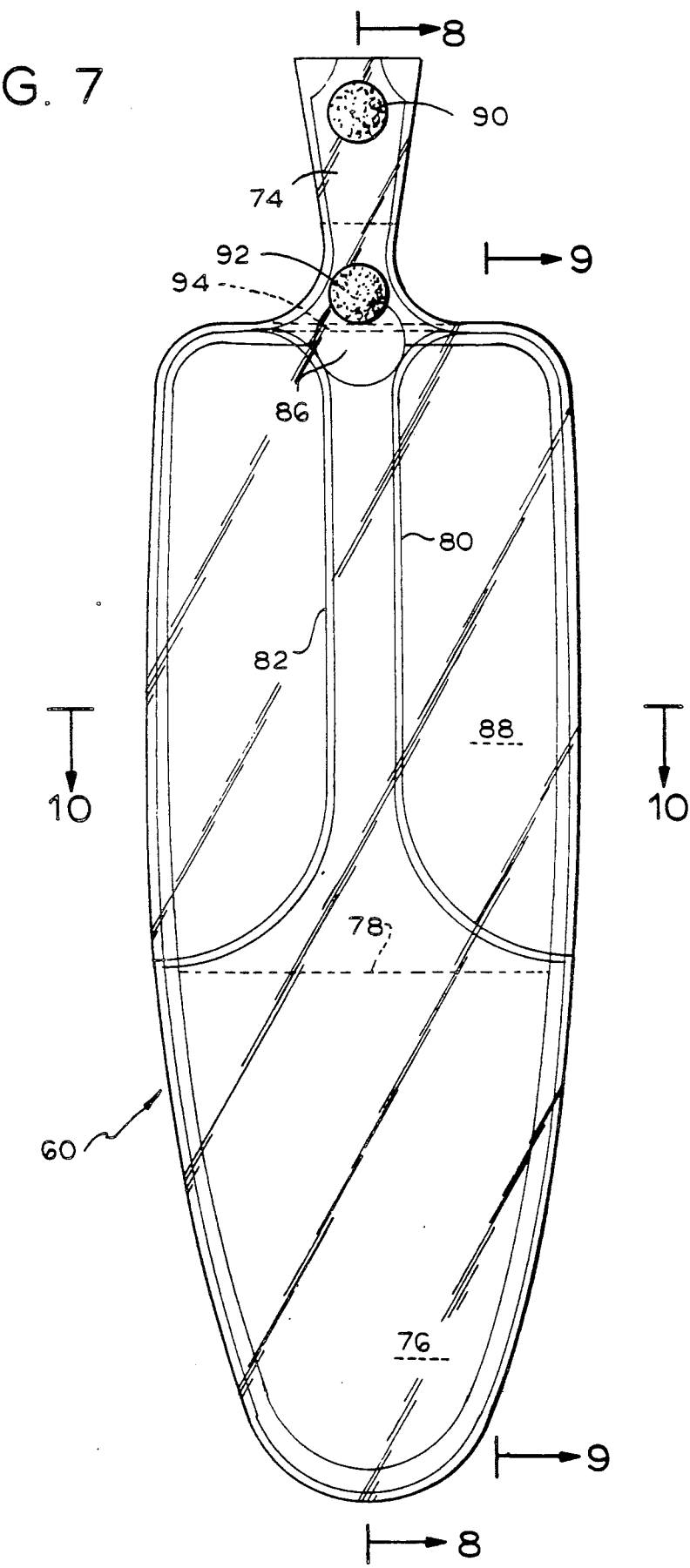
FIG. 7 is a view in elevation of the alternatively preferred embodiment of FIG. 6 a assembled.

In accordance with the present invention, the first chamber in unitary member 60 is formed coextensively with the bottom portions of plies 62, 64 and preferably is pre-inflated by positioning a first filler member or pad 76 of porous, compressible material (e.g. open cell urethane foam) between the plies before the latter are bonded together along their common peripheral extents as taught in my '920 patent. As best seen in FIGS. 6 and 7, the first filler member 76 has a shape and size conforming substantially to the bottom portions of plies 62, 64 and terminates in a relatively straight, horizontally extending upper boundary 78 defining the upper extremity of the first chamber.

Plies 62, 64 are also bonded together locally along a pair of seams 80, 82 (FIGS. 7) which extend inwardly from their intersection with the opposed edges of the plies immediately above upper boundary 78 of first filler member 76. Seams 80, 82 then extend arcuately upwardly substantially as shown in spaced relation to one another until they arcuately intersect the upper edges of plies 62, 64 on either side of the base portion defining integral valve extension 74. By this arrangement, a longitudinally extending thru-passage 84 is formed between plies 62, 64 connecting valve 74 with the upper portion of the first chamber. The cross-section of passage 84 is shown slightly exaggerated for purposes of clarity in FIG. 10.

Prior to bonding plies 62, 64 together along their peripheral extents and along seams 80, 82, an insulating member 86 preferably in the form of a thin disc of paper or TEFLON material is affixed by a suitable, known adhesive to the surface of ply 64 facing ply 62 in a position coinciding with the common upper edge of plies 62, 64 immediately below the extreme necked-down thoat portion of valve 74 as clearly shown in FIGS. 6-8. The insulating member 86 prevents plies 62, 64 from being welded or bonded together when ply 66 is subsequently joined to plies 62, 64 to form unitary member 60.

The second chamber in unitary member 60 is formed coextensively with substantially the entire extent of plies 64 and 66, and as is the case with the first chamber, preferably is preinflated. This is accomplished by positioning a second filler member 88 of the same material as filler member 76, having a shape and size conforming generally to that of both plies 64, 66 between the plies and then bonding ply 66 to ply 64 (and ply 62) along their common peripheral extents using known heat or electronic sealing methods.

It will be observed that the resulting unitary member 60 comprises a pair of pressurizable chambers divided by a common wall (ply 64) with one of the chambers extending coextensively with respect to substantially the entire member, and the other chamber extending only partially coextensively with respect to the member 60 and the first mentioned chamber, said other chamber being disposed in an overlapping, juxtaposed manner with respect to the bottom portion of said first chamber The unitary member 60 also includes valve means 74 for selectively inflating only the other chamber with the valve means being comprised in part by said common wall (see FIGS. 8).

In practice, the unitary member 60 of FIGS. 6-10 may be substituted for the inflatable airbags 28a, 28b, and 30a, 30b of the embodiment of FIGS. 1-5 by being attached directly to each sidewall member's inner surface 15a, 15b, respectively, using a suitable adhesive compound a pair of mating VELCRO fastener elements The unitary member is positioned relative to each sidewall member so that valve 74 extends above the upper edge of each sidewall member, and the overlapping juxtaposed chambers defined by filler members 76, 88 (i.e. the bottom portion of member 60) overlie VELCRO fasteners 24a, 24b and base member hinge end portions 18a, 18b. In such arrangement, it is preferable to place the side of member 60 defined as the smaller chamber (i.e filler member 76 and ply 62) against surfaces 15a, 15b so that the uninterrupted, smooth surface of the side defined by the larger chamber (i.e. filler member 88 and ply 66) faces oppositely and directly contacts the medial and lateral portions of the lower extremity, respectively.

As is true with respect to the supplemental airbags 30a, 30b of the initial embodiment of FIGS. 1-5, filler member 76 and the pressurizable chamber defined thereby in the lower portion of unitary member 60 is intended to focus maximum supporting pressure in the region of the ankle. Thus, for the same reasons given above in connection with the initial embodiment, it is preferred that filler member 76 have a greater transverse thickness as measured in the plane of FIGS. 8 and 9 than that of filler member 88. Without limiting the present invention, I have found that excellent results are achieved using an ankle brace having upstanding sidewall members about 10 inches in longitudinal extent, a filler member (small) having a transverse thickness of about 0.225 inches, and a filler member (large) having a transverse thickness of about 0.125 inches.

Nonetheless, it will be understood that the thickness of the small filler member i.e. member 76, may be made less where compensation to achieve the desired internal pressurization of the chamber defined by the smaller filler member is effected by increasing the tension in the bottom-most fastener strap 48d of brace 10 through circumferential tightening of the strap via suitable adjustment of the strap and of mating patch elements 50d and 56d. Because of this flexibility of adjustment, it is feasible for the filler members 76, 88 to have the same thickness which latter may range from about 0.1 inches to about 0.5 inches, with a thickness in the range from about 0.125 inches to about 0.3 inches being mostly preferred.

Also, it may be desirable to adjust the supporting pressure afforded by filler member 76 in its chamber from time to time. This may easily be accomplished using valve 74 to increase or decrease the internal pressure of the chamber. It will be noted in the alternatively preferred embodiment of FIGS. 6-10 that no such valve is provided in connection with the larger chamber defined by filler member 88, as any adjustment of the internal pressure of the larger chamber normally is not required in view of the excellent graduated compression effect achieved by the unitary member, and the adjustability afforded by using valve 74 in connection with the smaller chamber.

Finally, if desired, a pair of VELCRO mating fasteners 90, 92 may be affixed to the valve exterior 74 as shown in FIGS. 6 and 7 so that the valve may be folded upon itself and fastened in place.

An important advantage of the preferred embodiment of FIGS. 6-10 is the ease and relatively reduced cost of manufacture of unitary member 60. Thus, during fabrication, plies 62, 64, and 66 are coextensively aligned relative to one another with filler member 76 appropriately positioned between plies 62 and 64, and filler member 88 appropriately positioned between plies 64 and 66. The stacked arrangement is then engaged by a suitable sealing die and bonded together along the entire peripheral extent thereof and along seams 80 and 82. Owing to placement of insulation disc 92 in the throat of valve 74 on inner surface of ply 64 facing ply 62, the top edge weld or bonded seam 92 between plies 66 and 64 will not print through to ply 62. Likewise, due to the insulating effect of filler member 88, seams 80 and 82 will merely bond plies 62 and 64 together accordingly, but will not print through to ply 66. If desired, the foregoing assembly operation may be accomplished in two steps, i.e. plies 62 and 64 being bonded together initially followed by the step of bonding ply 66 to the partially completed member 60.

Without departing from the principals of the present invention, still other variations in construction of the unitary member are possible Thus, turning now to the further alternatively preferred embodiments of FIGS. 11-16, where reference numeral 60′ generally represents the unitary member and where like reference numerals represent similar elements, there is shown an arrangement where the valve integrally formed by two of the plies permits selective pressurization (or depressurization) of the second chamber rather than the first chamber. As in the case of unitary member 60 (FIGS. 6-10), unitary member 60′ comprises three relatively thin sheets or plies 62′, 64′ and 66′ coextensively joined or bonded together along their common peripheral extents to form a pair of pressurizable chambers interiorly thereof, with each ply being fabricated from an air-impervious, tough, flexible material such as vinyl plastic, for example, and cut to the shape substantially shown on a conventional die cutting press.

Figure 12:
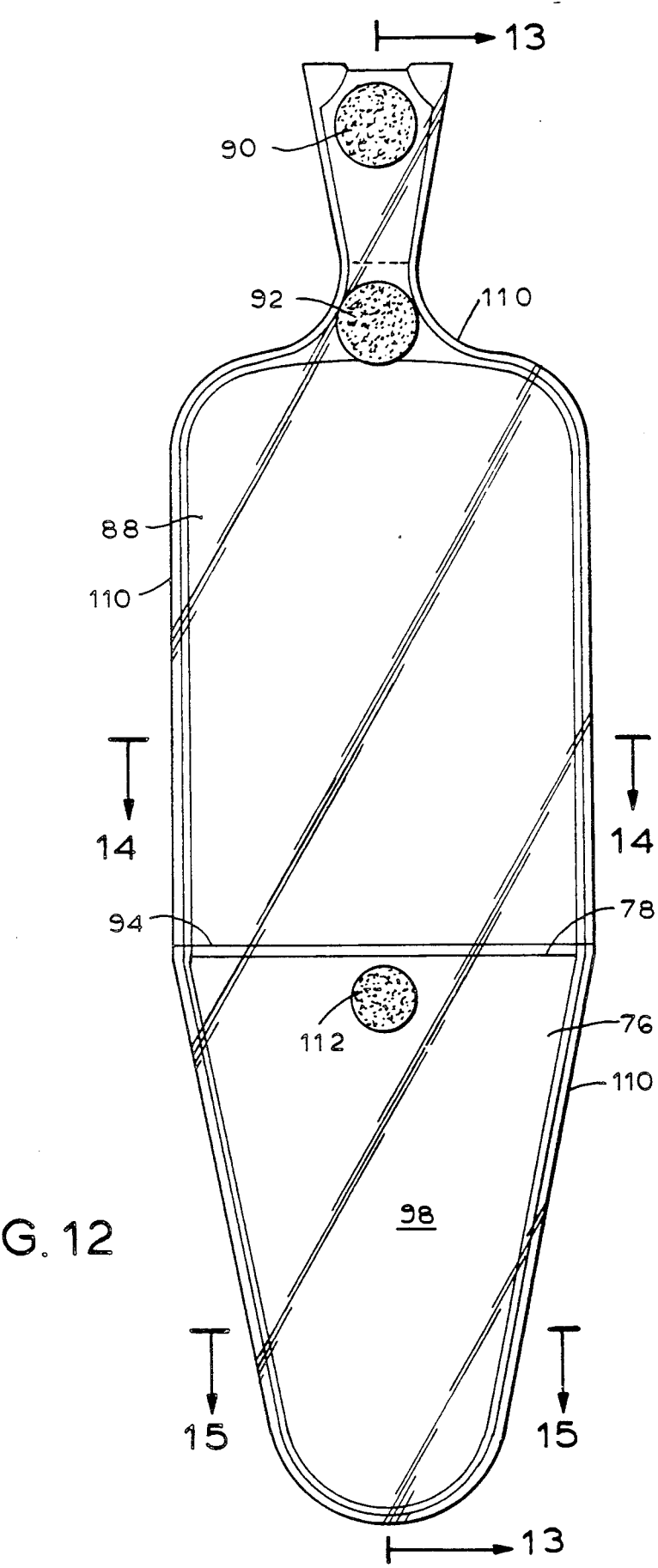
FIG. 12 is a view in elevation of the alternatively preferred embodiment of FIG. 11 as assembled.

Ply 62′ however is shaped in such a manner that it may be folded about a medial line or crease 94 to form a pocket or sleeve comprising a pair of opposed mirror-imaged sections 96, 98 for receiving filler member 76 therebetween such that the upper boundry or terminal edge 78 is juxtaposed proximally to crease 94 and the sleeve and filler member may be positioned coextensively and congruently with respect to the bottom portions of plies 64′ and 66′ to form the first chamber as best viewed in FIGS. 12 and 13.

The second chamber disposed in unitary number 60′ is formed coextensively with substantially the entire extent of plies 64′ and 66′, and also preferably is pre-inflated by positioning the second filler member 88 which has a shape and size conforming generally to that of both plies, and which is of the same material as filler member 76 (e.g. open cell urethane foam) between plies 64′ and 66′ substantially as shown, before plies 64′, 66′ and folded ply 62′ are bonded together along their common peripheral extents as will be explained more fully below.

It will be noted that plies 64′, 66′ are mirror images of one another and include integral extensions 64′a, 66′a projecting upwardly with respect to their topmost edges, respectively. The extensions 64′a, 66′a, in turn, are folded along creases 100, 102 to define a pair of confronting end flaps 104, 106. Thus, when plies 64′, 66′ are bonded together congruently in the manner described more fully in my prior '920 patent, the integral extensions 64′a and 66′a and end flaps 104 and 106 form a self-sealing valve member 108 (FIG. 12) adapted to seal any air in the second chamber formed interiorly of the joined plies 64′, 66′ thereby preventing loss of internal pressurization As further taught in the '920 patent, integral valve 108 may selectively be opened as, for example, by a suitably shaped plastic tube inserted between confronting flaps 104, 106 to admit or exhaust air from the second chamber.

The provision of the integral valve 108 to permit adjustment in internal pressurization of the second chamber greatly simplifies and lowers the cost of manufacturing the unitary member 60′ of FIGS. 11-15. Thus, during fabrication, plies 64′ and 66′ first are coextensively and congruently aligned relative to one another with filler member 88 placed in appropriate registration therebetween. Ply 62′ may then be folded about crease 94 and filler member 76 placed in coextensive and congruent position between sections 96, 98. The resulting sandwich comprising ply 62′ (i.e. sections 96, 98) and filler member 76 next is positioned congruently with respect to the bottom portion of the confronting sandwich formed by ply 64′, filler member 88, and ply 66′ such that the peripheral margins of the opposed sandwiches are in registration and crease 94 extends substantially horizontally along the transverse extent of unitary member 60′ as viewed in FIG. 12. A suitably configured heat or electronic sealing die may then be employed to engage the entire stacked arrangement comprising the aligned confronting sandwiches of plies and filler members thus joining them together along peripheral seam or weld 110 in a single step.

From the above, it will be appreciated that the resulting unitary member 60′ comprises a pair of pressurizable chambers divided by a common wall comprising juxtaposed ply 64′ and section 96 of ply 62′ with one of the chambers extending coextensively with respect to substantially the entire unitary member, and the other chamber extending only partially coextensively with respect to the first mentioned chamber, i.e. in an overlapping, juxtaposed manner with respect to the bottom portion of said first chamber. The unitary member 60' also includes valve means 108 for selectively inflating or adjusting the internal pressurization of only the other chamber with the valve means being comprised in part by said common wall (see FIG. 13).

In practice, it will be appreciated that the unitary member 60' of FIGS. 11-16 also may be substituted for the inflatable airbags 28a, 28b, and 30a, 30b of the embodiment of FIGS. 1-5 by being attached directly to each sidewall member's inner surface 15a, 15b, respectively, using a suitable adhesive compound or if desired, mating VELCRO fasteners, one element of which, identified by reference numeral 112, may be attached to the outwardly facing surface of section 98 of ply 62' and the other element of which may be affixed by adhesive to the inner surface of the corresponding sidewall member. The unitary member 60', in either case, is positioned and attached relative to each sidewall member so that valve 108 extends above the upper edge of each sidewall member, and the overlapping juxtaposed chambers defined by filler members 76, 88 (i.e. the bottom portion of member 60') overlie VELCRO fasteners 24a, 24b and base member hinge portions 18a, 18b. Here again, it is preferable to place the side of member 60' defined as the smaller chamber side (i.e. filler member 76 and section 98 of ply 62') against surfaces 15a, 15b so that the uninterrupted, smooth surface of the side defined by the larger chamber (i.e., filler number 88 and ply 66') faces oppositely and directly contacts the medial and lateral portions of the lower extremity, respectively, when brace 10 is fitted thereabout.

When valve member 108 is located in such a manner to permit selective pressurization or depressurization of the other or larger chamber defined by filler member 88, the bottom portion of the filler member 88 coextensive and congruent with filler member 76 may be dispensed with. This yet further variation of the alternatively preferred embodiment of FIGS. 11-15 is shown in FIG. 16, i.e. filler member 88 extends between a top edge 114 and a bottom edge 116 and is generally vertically aligned with the lower or smaller filler member 76 as viewed in FIG. 16. If such a modified arrangement is desired, the folded ply 62' may be eschewed in favor of a smaller ply 118 substantially coextensive with the smaller filler member 76 and bonded to the inside surface of ply 64' along a seam or weld 120 defined by the common peripheral extents of plies 118 and 64'. After plies 118 and 64' are bonded together accordingly, a second bonding/sealing operation is necessary to bond ply 66' to ply 64' and ply 118 along seam 110 after the upper filler member 88 has been positioned substantially as shown in FIG. 16.

It will thus be seen that the alternative embodiments of FIGS. 6-10 and of FIGS. 11-16 are capable of achieving all of the advantages of the initial embodiment of FIGS. 1-5, yet offer obvious added improvement in terms of simplicity of construction, reduced bulk, and a more aesthetic appearance.

As used herein, the term "lower extremity" should be interpreted broadly to include the foot, the ankle, and the lower leg.

Obviously, many other modifications and alterations of the present invention will occur to these with ordinary skill. Accordingly, the present invention should be limited only by the spirit and scope of the appended claims.

I claim:

1. An ankle brace comprising an outer shell member, said shell member having a pair of opposed elongated sidewall support members attached together at the distal ends thereof by a flexible web, a pair of supporting cushion members on said sidewall members, and fastening means adapted to fasten said sidewall members about the leg with the cushion members between the sidewall members and the leg and with the flexible web passing under the sole of the foot, wherein each sidewall member has a transverse and longitudinal extent sized to confront only the opposed sides of the leg, respectively, wherein at least one of said supporting cushion members in said pair comprises a first inflatable aircell, said first aircell being substantially of the same transverse and longitudinal dimensions as its corresponding sidewall member, and means for achieving both graduated compression with the greatest pressure in the ankle region, and pulsating pressure during ambulation, said means comprising a second inflatable aircell, said second aircell being of lesser extent than said first aircell and being juxtaposed in an overlapping manner with said first aircell on the distal end portion of said corresponding sidewall member adjacent said flexible web, said second inflatable aircell having substantially the same transverse extent as said sidewall member distal end portion and having a longitudinal extent substantially less than the longitudinal extent of said first aircell such that said second aircell and the overlapped portion of said first aircell are adapted to confront the side of the leg in the region of the ankle and the non-overlapped portion of said first aircell is adapted to confront the side of the leg above the ankle when said shell member is fastened about said leg by said fastening means.

2. The ankle brace of claim 1 wherein said second aircell is disposed in an overlapping manner between said sidewall member and said first aircell.

3. The ankle brace of claim 1 wherein said second aircell is approximately one-half the size of said first aircell.

4. The ankle brace of claim 1 wherein a pair of said second aircells of lesser extent is disposed on said pair of sidewall support members, respectively.

5. The ankle brace of claim 1 wherein said first inflatable aircell comprises valve means for selectively admitting pressurized air to said first aircell.

6. The ankle brace of claim 1 wherein either said first aircell or said second aircell comprises inflatable means in the form of a porous, compressible member disposed interiorly thereof.

7. The ankle brace of claim 1 wherein said first aircell and said second aircell are joined together to form a unitary aircell having a first chamber defining said first aircell and a second chamber defining said second aircell.

8. The ankle brace of claim 7 wherein said first chamber comprises valve means for selectively admitting pressurized air thereto.

9. The ankle brace of claim 7 wherein said unitary aircell consists of a plurality of flexible, plastic sheets superimposed and bonded together along their peripheral extents, said first chamber comprising first and second sheets of substantially the same size and shape as said sidewall member, and said second chamber comprising a third sheet of substantially the same size and shape as said sidewall member folded about itself to form a transverse fold extending substantially perpendicular to the longitudinal boundaries of said first and second sheets intermedially of the longitudinal extent of said first and second sheets.

* * * * *